United States Patent [19]
Arai

[11] Patent Number: 5,784,429
[45] Date of Patent: Jul. 21, 1998

[54] DENTAL PANORAMIC X-RAY IMAGING APPARATUS

[75] Inventor: Yoshinori Arai, Tokyo, Japan

[73] Assignee: J. Morita Manufacturing Corporation, Kyoto, Japan

[21] Appl. No.: 886,956

[22] Filed: Jul. 2, 1997

Related U.S. Application Data

[63] Continuation of Ser. No. 752,592, Nov. 21, 1996, abandoned.

[30] Foreign Application Priority Data

Nov. 22, 1995  [JP]  Japan .................................. 7-304697

[51] Int. Cl.$^6$ ...................................................... H05G 1/64
[52] U.S. Cl. ............................ 378/38; 378/39; 378/98.8
[58] Field of Search ................................ 378/38–40, 4, 378/21, 23, 24, 25, 26, 901, 98.5, 98.6, 98.8, 98

[56] References Cited

U.S. PATENT DOCUMENTS 5,214,686  5/1993  Webber .................................. 378/40

FOREIGN PATENT DOCUMENTS

H2-84942   3/1990  Japan .
H2-29329   6/1990  Japan .
H4-144548  5/1992  Japan .

Primary Examiner—Don Wong
Attorney, Agent, or Firm—Koda & Androlia

[57] ABSTRACT

A dental panoramic X-ray imaging apparatus which can use wide X-ray beams and obtain a tomographic image with a reduced level of blur is provided.

By using image information detected by an X-ray image detector, tomographic images which are eight in total and correspond to plural tomographic planes arranged at predetermined intervals along the X-ray irradiation direction, for example, eight tomographic planes are calculated. Next, attention is paid to a specific one of the eight tomographic images, and a convolution process is conducted by using image information of one or more of the tomographic images, thereby removing blur from the specific tomographic image. Furthermore, the blur removal is conducted on two or more of the tomographic images, and the tomographic images from which blur is removed are summed each other so as to obtain a final synthesized tomographic image.

2 Claims, 9 Drawing Sheets

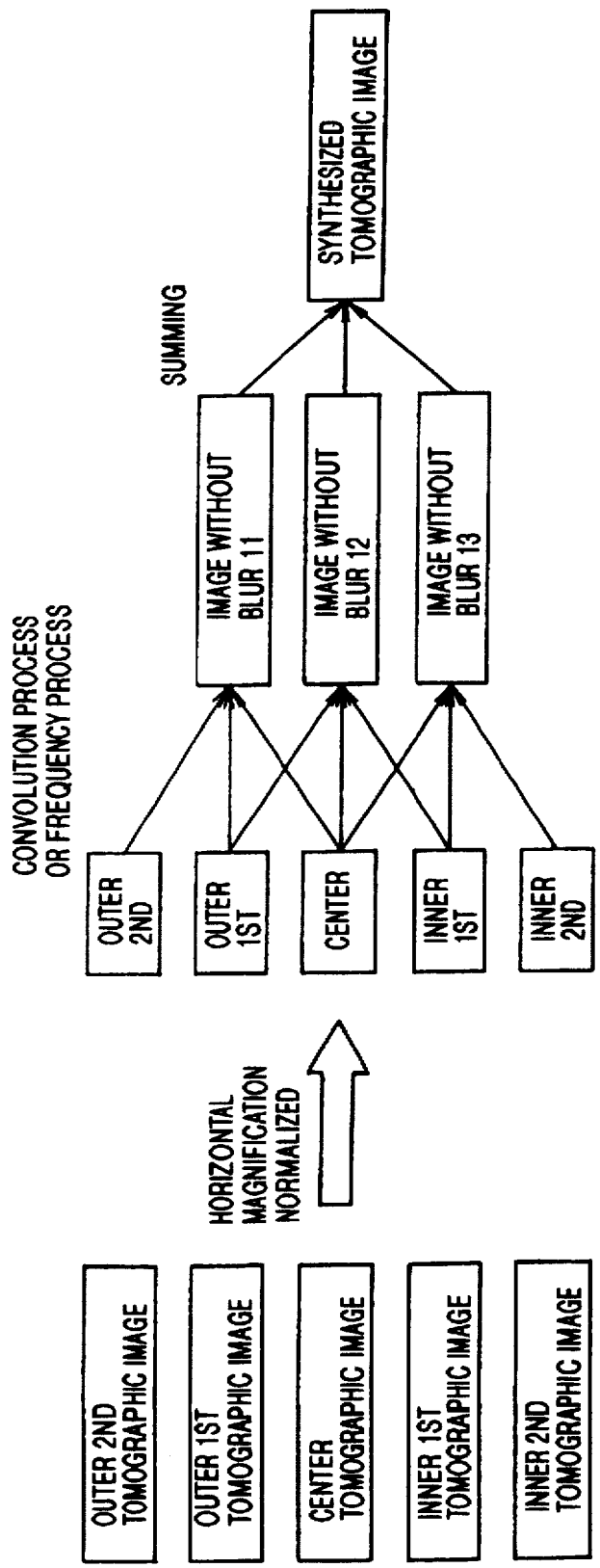

DENTAL PANORAMIC X-RAY IMAGING APPARATUS

This application is a continuation of application Ser. No. 08/752,592, filed Nov. 21, 1996, now abandoned.

BACKGROUND OF THE INVENTION

1. Field of the Invention

The present invention relates to a dental panoramic X-ray imaging apparatus which can obtain information on an arbitrary curved tomography plane as a two-dimensional panoramic image.

2. Description of the Related Art

Conventionally, a digital panoramic X-ray imaging apparatus is proposed in which information of a dental arch is imaged by using an X-ray image sensor for converting X-ray images into electric signals, in place of an X-ray film, the image information is stored in a memory or the like, and a predetermined calculation process is then performed to calculate a tomographic image corresponding to an arbitrary tomographic plane (Japanese Patent Publication (Kokoku) No. HEI2-29,329). According to the apparatus, when image information of the dental arch is once stored, a desired tomographic plane can be designated thereafter to obtain an arbitrary tomographic image. In other words, the proposed apparatus can produce various tomographic images from only one X-ray imaging process.

Another digital panoramic X-ray imaging apparatus which employs a technique of obtaining a tomographic image by means of such a calculation process is proposed (Japanese Patent Publication (Kokai) No. HEI4-144,548). In the apparatus, a first tomographic image corresponding to a first tomographic plane elongating along the dental arch which is the object to be diagnosed is calculated, a second tomographic image corresponding to a second tomographic plane including the vertebrae cervicales, the mandibula edges, etc. which will obstruct image observation is then calculated, the obtained second tomographic image is subjected to a calculation process such as the inverse projection conversion, and the obstacle shadow image is subtracted from the first tomographic image, thereby obtaining a tomographic image in which the obstacle shadow is reduced in level.

However, such digital panoramic X-ray imaging apparatuses of the prior art can obtain only one tomographic image along a specific tomographic plane. For a dental arch of a considerably large thickness, therefore, it is impossible to sufficiently obtain information.

In order to obtain an image with a reduced level of blur, narrow beams in which the width of X-ray beams is reduced must be used. This causes the use efficiency of X-rays to be lowered and the period required for imaging tends to be prolonged.

SUMMARY OF THE INVENTION

It is an object of the invention to provide a dental panoramic X-ray imaging apparatus which can use wide X-ray beams and obtain a tomographic image with a reduced level of blur.

The dental panoramic X-ray imaging apparatus of the invention comprises: an X-ray source for irradiating an object with X-rays;

X-ray image detecting means for detecting an image of X-rays which have passed through the object;

swivel means for integrally swiveling the X-ray source and the X-ray detecting means around the object;

image storing means for storing image information output from the X-ray detecting means during a period when the swivel means operates; and image processing means for, on the basis of image information stored in the image storing means, forming a tomographic image along a desired tomographic plane and conducting a calculation process on the tomographic image, wherein plural tomographic images corresponding to plural tomographic planes which are arranged at predetermined intervals along a direction of the X-ray irradiation are calculated, a convolution process or a frequency process is conducted on a specific tomographic image by using image information of at least one of the tomographic images, and thereby blur from the specific tomographic image is removed.

According to the invention, a convolution process or a frequency process is conducted by using plural tomographic images, whereby a tomographic image which is free from blur can be obtained. The frequency process is a process in which, after the FFT (Fast Fourie Transform) has been conducted, an image is appropriately weighted in a frequency space, and the image is then returned to the original by conducting the inverse FFT. In the case where an X-ray imaging process is conducted by using wide X-ray beams, even when tomographic images are blurred, a clear tomographic image can be obtained by the above-mentioned removal of blur.

The use of wide X-ray beams produces advantages such as: 1) influences of obstruction shadows such as the vertebrae cervicales can be reduced; 2) the use efficiency of X-rays is improved and the current of an X-ray tube can be reduced, thereby lowering the burden of the X-ray tube; and 3) X-ray detecting means having a large imaging area can be used and hence the imaging efficiency is improved.

The invention is characterized in that removal of blur is conducted on two or more images of the tomographic images, and the tomographic images from which blur has been removed are summed each other, thereby obtaining a synthesized tomographic image.

According to the invention, since tomographic images from which blur is removed are summed each other to obtain a synthesized tomographic image, it is possible to obtain an X-ray tomographic image which has a reduced level of noises and higher sharpness.

BRIEF DESCRIPTION OF THE DRAWINGS

Other and further objects, features, and advantages of the invention will be more explicit from the following detailed description taken with reference to the drawings wherein:

FIG. 12 is a flowchart showing a specific example of the process of removing blur according to the invention.

DETAILED DESCRIPTION OF THE PREFERRED EMBODIMENTS

Figure 1:
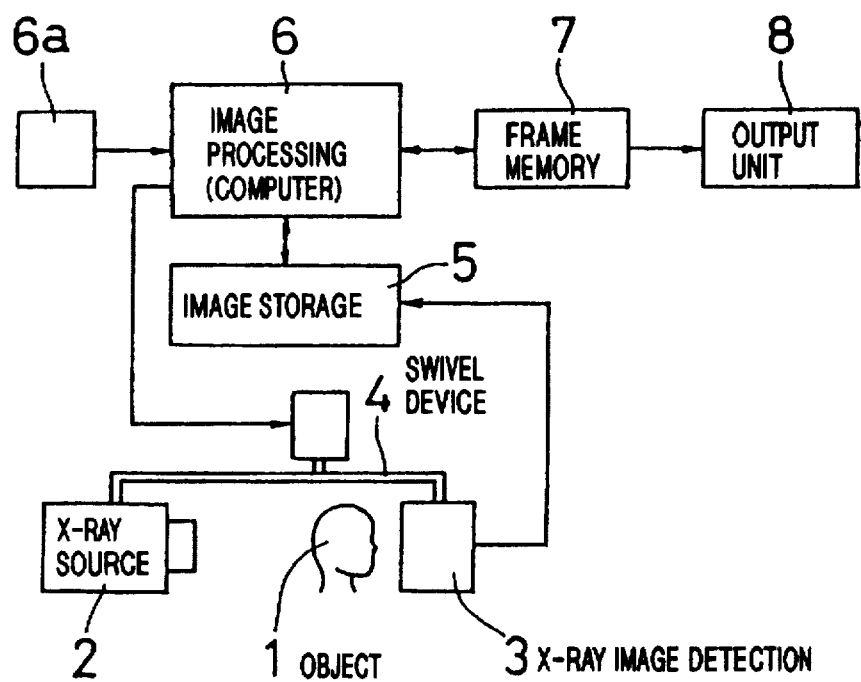
FIG. 1 is a block diagram showing an embodiment of the invention.

Now referring to the drawings, preferred embodiments of the invention are described below.

FIG. 1 is a block diagram showing an embodiment of the invention. An X-ray source 2 and an X-ray image detector 3 are disposed so as to oppose to each other with an object 1 between them, and attached to the ends of an arm of a swivel device 4, respectively. The X-ray source 2 is provided with a primary slit and generates X-ray beams which are vertically elongated and parallel with the rotation axis, thereby irradiating the object 1 with the X-ray beams.

The X-ray image detector 3 detects two-dimensionally the X-ray image passed through the object 1 as a slit image which is vertically elongated, and converts the image into electric signals. A well known X-ray image sensor may be used as the X-ray image detector 3. For example, such X-ray image sensors include an X-ray camera having a scintillator which converts an X-ray into visible light, and a SIT (Silicon Intensified Tube) which converts an image formed on the scintillator into electric signals with a high sensitivity, an X-ray CCD (Charge Coupled Device) sensor which uses a semiconductor device in place of the SIT, MOS (Metal Oxide Semiconductor) sensor, and an X-ray fluorescent intensifier.

The arm of the swivel device 4 is rotatably supported, and rotated at a constant angular velocity in accordance with a driving signal supplied from an image processing unit 6. An image storage unit 5 continuously stores image information of the object 1 output from the X-ray image detector 3 during a period when the arm is rotated. As the image storage unit, useful are a VTR (Video Tape Recorder), a video signal recording apparatus such as an optical disk, or a magnetooptical disk, and a semiconductor memory device such as a RAM (Random Access Memory) with a large capacity.

The image processing unit 6, which may be realized by a computer or the like, conducts the calculation process on the basis of image information stored in the image storage unit 5, and also controls the operation of the whole of the apparatus. An input device 6a such as a keyboard through which the user inputs data is connected to the image processing unit 6. A panoramic image obtained by the image processing in the image processing unit 6 is stored in a frame memory 7 and supplied to an output unit 8, including an image display device such as a CRT or a liquid crystal display device, or a hard copy device which prints out the image.

Figure 2:
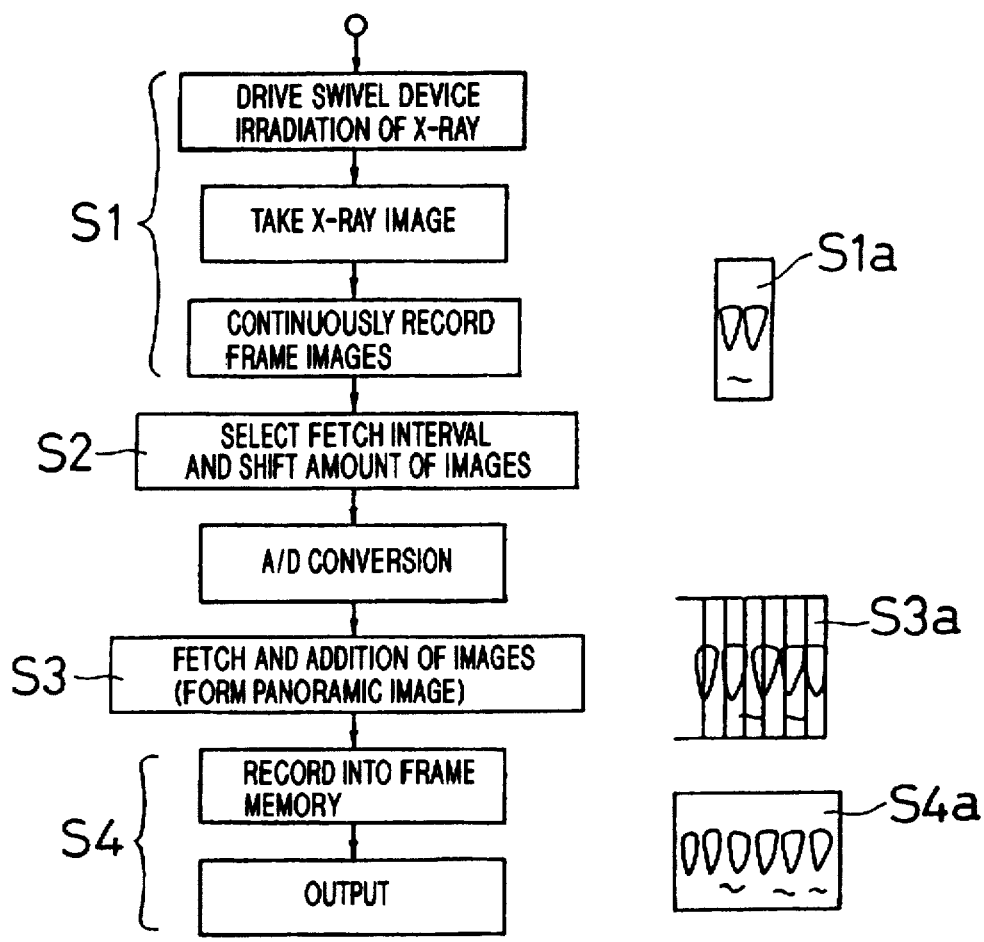
FIG. 2 is a flowchart showing the operation procedure of the whole apparatus.

FIG. 2 is a flowchart showing the operation procedure of the whole apparatus. While the swivel device 4 is driven, the X-ray source 2 irradiates the object 1 with X-rays, and the X-ray image detector 3 receives X-rays passed through the object 1 and converts the obtained X-ray image information into electric signals of a frame image. For example, the electric signals have the same signal format as that of a video signal used in a television system. The images are continuously stored in the image storage unit 5 at the rate of 30 images per second (step S1). The frame image is formed as a vertically elongated slit image which corresponds in shape to the X-ray slit beams. When the X-ray image detector is moved a half of the circumference of the object 1 during a period of 30 seconds, for example, a series of 900 frame images are obtained. Such frame images are not required to have a continuous signal form such as that of the above-mentioned video signal. For example, the imaging process may be done intermittently in a short cycle and resulting images may sequentially be converted into electric signals.

Next, the fetching interval at which frame images arranged in certain time intervals are fetched from a series of frame images continuously stored in the image storage unit 5, and the distance or the shift amount for summing the fetched frame images while shifting their positions in the width direction of the slit image by a predetermined distance are selected (step S2). Corresponding frame images are sequentially fetched in the form of a digital signal at the fetch interval, and then subjected to the summing process while shifting the positions in accordance with the selected shift amount (step S3). The fetch interval and the shift amount can be arbitrarily selected. In accordance with this, a panoramic image of a specific tomographic plane is obtained as a result of the above-mentioned summing process. The panoramic image is stored in the frame memory 7, and, as required, displayed on the output unit 8 or output in the form of a hard copy (step S4).

The symbols S1a, S3a, and S4a schematically show examples of the images obtained in the steps.

The principle of the above-mentioned technique of obtaining a panoramic image of a specific tomographic plane in accordance with the fetch interval and the shift amount is identical with that of the technique in which, in a conventional film panoramic X-ray imaging apparatus, an X-ray source and a film are relatively moved at a predetermined ratio so as to obtain a panoramic image of a specific tomographic plane. In contrast, the digital system is different in that a panoramic image of an arbitrarily tomographic plane can be adequately formed by selecting the fetch interval and the shift amount after the imaging process.

Figure 3:
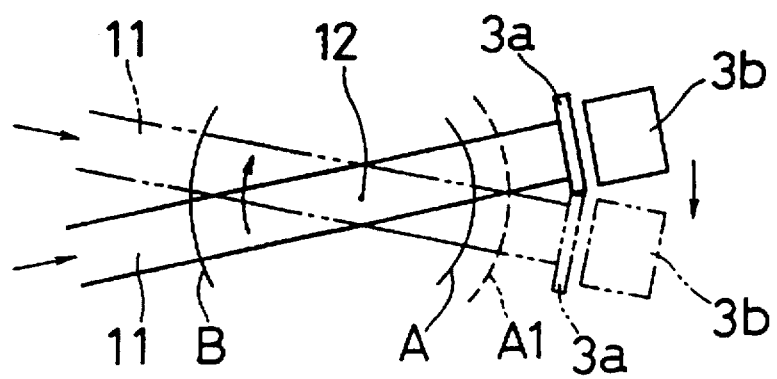
FIG. 3 is a diagram illustrating the principle of the panagraphy.

FIG. 3 is a diagram illustrating the principle of the panagraphy. Assuming that X-ray beams 11 are swiveled around the swivel center 12 in a clockwise direction, an image of an object in a tomographic plane A is projected to an X-ray image detection screen 3a of the X-ray image detector 3 which is swiveled together with the X-ray beams 11, and traverses the X-ray image detection screen 3a in the direction from the left to the right as seen from an imaging device 3b. Similarly, also an image of an object in another tomographic plane A1 is projected to the X-ray image detection screen 3a and traverses the screen in the same direction. In this case, however, the moving speed of the image in the traverse is higher than that of the image of the tomographic plane A because the tomographic image is separated from the swivel center 12 by a greater distance. When the fetch interval and the shift amount are selected in accordance with the moving speeds of these images, therefore, a panoramic image of the object in the tomographic plane A or A1 in synchronization with the moving speed can be formed.

When the fetch interval and the shift amount are constant, the resulting tomographic image has an arcuate shape as shown in FIG. 3. However, the fetch interval and the shift amount are not necessary to be constant in one processing. When they are changed in relation to the movement of the swivel center of the X-ray beams, a similar panoramic image can be obtained even in the case of a tomographic plane such as a dental arch in which the curvature is changed depending on the position.

The fetch interval and the shift amount may be selected in accordance with results of a detection process in which a series of frame images continuously stored in the image storage unit 5 are reconstructed and the speed at which the objective image moves in the reconstructed image is detected. In other words, although unclear, images of objects through which X-rays have passed appear in reconstructed images, and hence it is possible to know the moving speed of the objective image. When the speed is measured, therefore, the setting values of the fetch interval and the shift amount which are adequate for obtaining a panoramic image of the objective tomographic plane can easily be calculated. The selected fetch interval and shift amount are input to the image processing unit 6 through the input device 6a such as a keyboard.

In this way, a panoramic image of an arbitrary tomographic image can be reconstructed by conducting only one X-ray imaging process.

Next, an example in which a panoramic image of an arbitrary tomographic image is reconstructed by subjecting an X-ray CCD sensor to the TDI (Time-Delay Integration) driving will be described.

Figure 4:
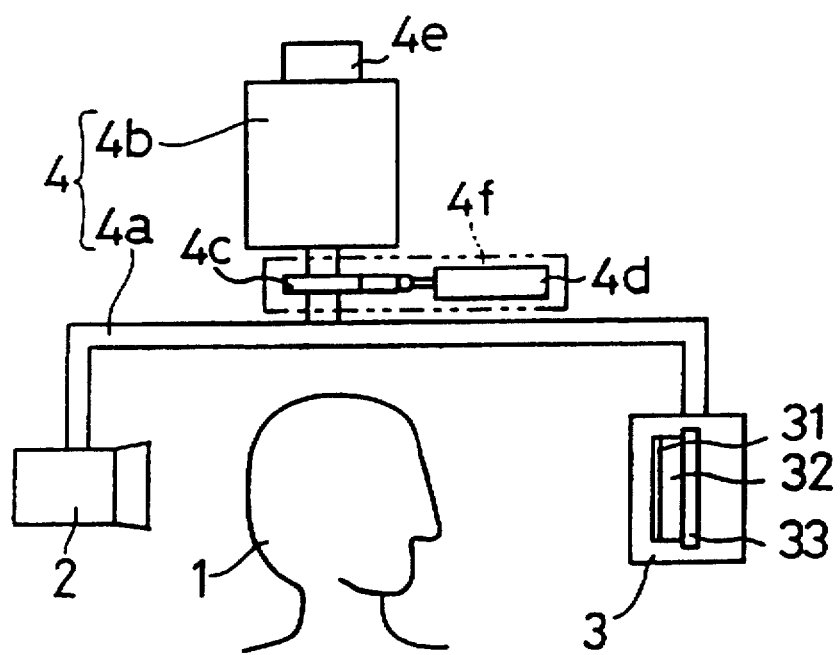
FIG. 4 is a diagram of a panoramic X-ray imaging apparatus using an X-ray CCD sensor.

FIG. 4 is a diagram of a panoramic X-ray imaging apparatus using an X-ray CCD sensor. An object 1 such as the head of a human being is positioned in a radiation path of X-rays between the X-ray source 2 and the X-ray image detector 3 which are disposed so as to oppose to each other. The X-ray source 2 and the X-ray image detector 3 are attached to the ends of an arm 4a which is rotatable. The X-ray image detector 3 comprises a scintillator 31 which converts X-rays impinging thereon into visible light, an optical fiber plate (abbreviated as "FOP") 32 which guides an image of the scintillator 31, and a CCD device 33 of, for example, the FFT (Full Frame Transfer) type which converts the image guided by the optical fiber 32 into electric signals. The arm 4a is rotated by an arm motor 4b. The rotating angle of the arm 4a is detected by an angle detector 4f. The angle detector 4f comprises a cam 4c attached to the rotation shaft of the arm motor 4b, and a potentiometer 4d in which a movable contact is moved by the cam 4c. The angular velocity of the rotation of the arm 4a is detected by a tachometer generator 4e.

Figure 5:
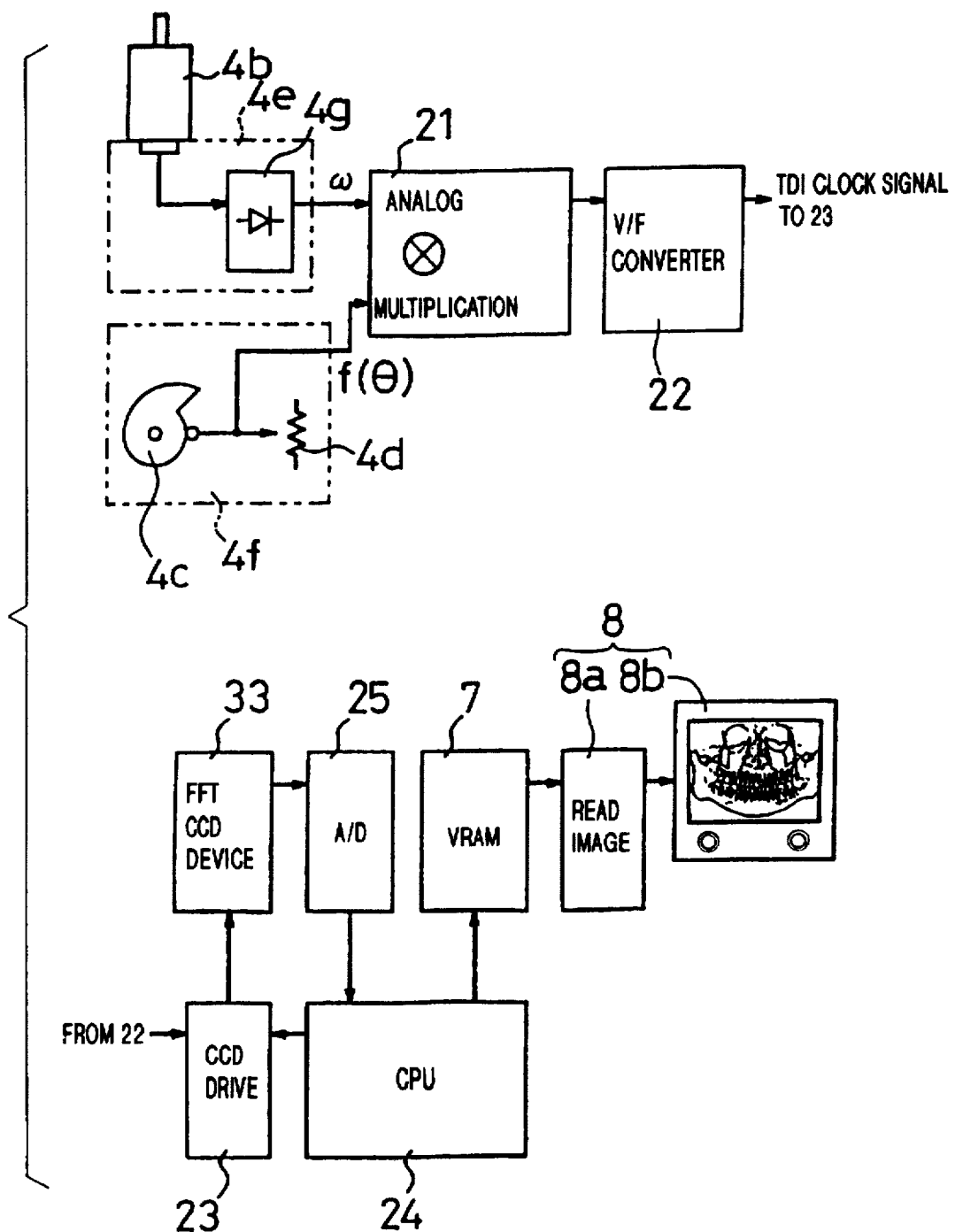
FIG. 5 is a block diagram showing the electrical configuration of the apparatus of FIG. 4.

FIG. 5 is a block diagram showing the electrical configuration of the apparatus of FIG. 4. The image taken by the CCD device 33 is subjected to accumulation in accordance with the TDI method by a CCD driving circuit 23 in which the operation timing is controlled by a CPU 24. The image signal is converted into a digital signal by an A/D (Analog/Digital) converter 25, and then supplied to the CPU 24. The CPU 24 writes the image signal into a frame memory 7 such as a VRAM. The image written into the frame memory 7 is read out by an image reading circuit 8a, and then displayed as a panoramic X-ray tomographic image on an image display device 8b.

A TDI clock signal for driving the CCD device 33 is obtained by multiplying an angular velocity ω output from the tachometer generator 4e with a function f(θ) of an angle θ output from the angle detector 4f by an analog multiplier 21, and frequency-converting the result of the multiplication by a voltage/frequency (hereinafter, abbreviated as "V/F") converter 22. The shape of the cam 4c of the angle detector 4f is set on the basis of the relationship between the film feed speed and the rotating angle θ of the arm. The tachometer generator 4e incorporates a rectifying circuit 4g which converts a signal corresponding to the angular velocity ω obtained as an AC signal into a voltage level.

Figure 6:
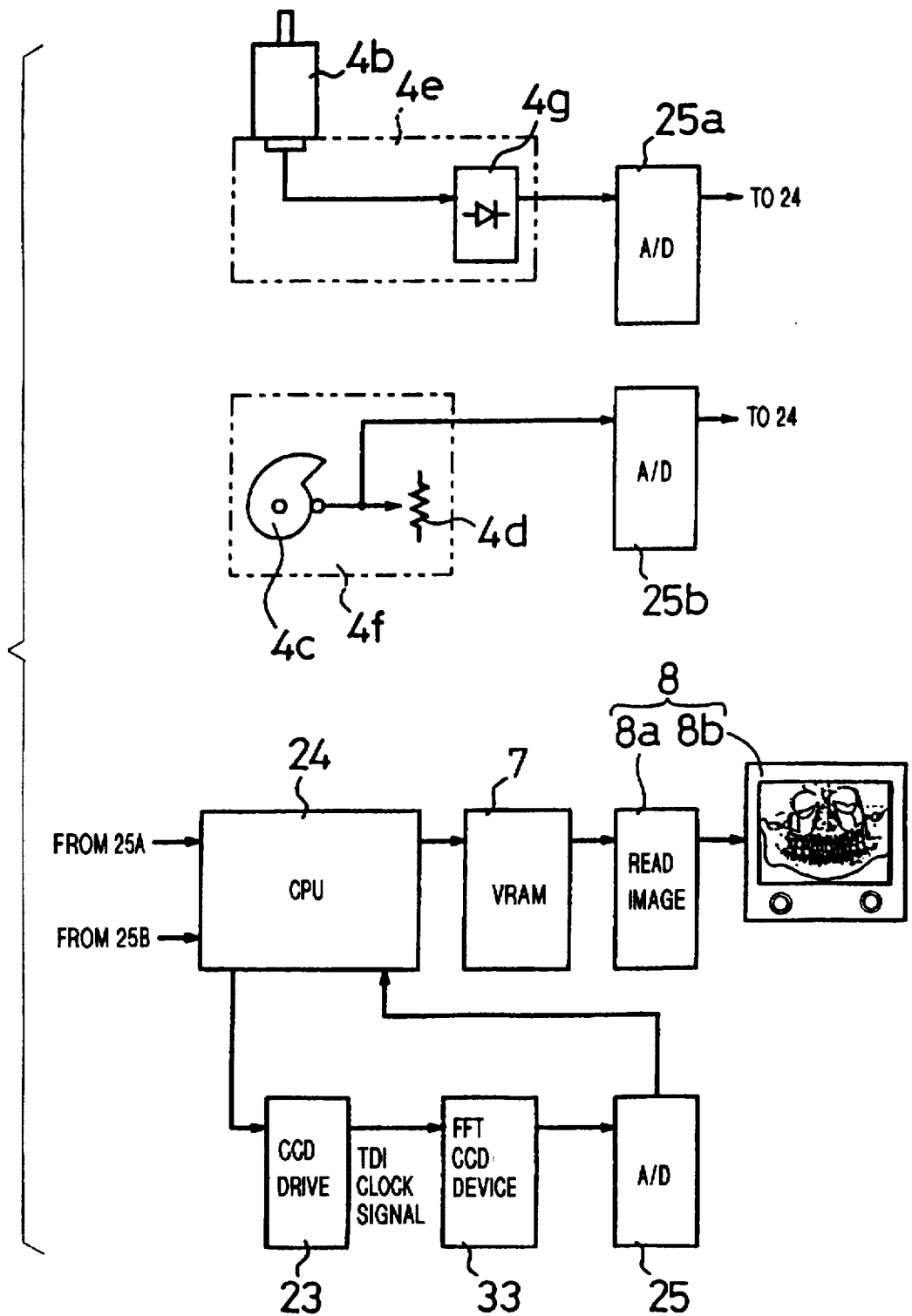
FIG. 6 is a block diagram showing another example of the electrical configuration.

FIG. 6 is a block diagram showing another example of the electrical configuration. In the example, the frequency of the TDI clock signal is calculated by a digital calculating process conducted by the CPU 24. The components corresponding to those of FIG. 5 are designated by the same reference numeral.

Values of the function f(θ) are set in the form of table data in the memory of the CPU 24. The outputs of the angle detector 4f and the tachometer generator 4e are digital-converted by A/D converters 25b and 25a, and then supplied to the CPU 24. In accordance with preset programs, the CPU 24 calculates $F=1/k \times f(\theta) \times \omega/d$ where F is the frequency of the clock signal, k is a constant, f(θ) is a value of the function f(θ) which determines the tomography orbit, and d is the width of one pixel, and performs processes and controls for generating the TDI clock signal.

Next, an example in which an X-ray CCD sensor is subjected to the TDI (Time-Delay Integration) driving will be described and panoramic images of plural tomographic images are reconstructed in one X-ray imaging process will be described.

Figure 7:
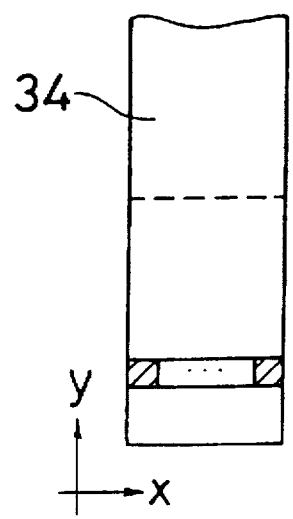
FIG. 7 is a diagram showing relationships between a secondary slit 34 and the imaging area of a CCD device 33 which are disposed in an X-ray image detector 3.
Figure 8:
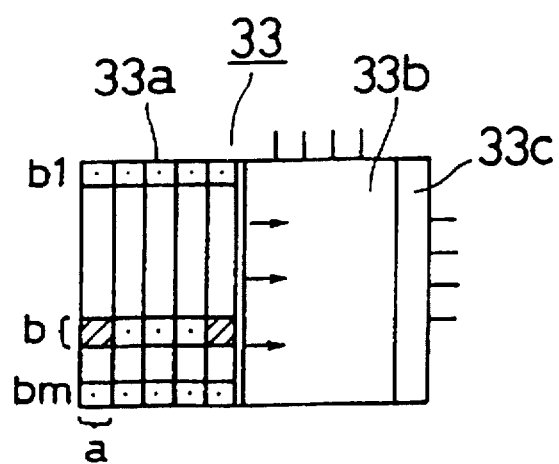
FIG. 8 is a diagram showing relationships between the secondary slit 34 and the imaging area of the CCD device 33 which are disposed in the X-ray image detector 3.

FIGS. 7 and 8 are diagrams showing relationships between a secondary slit 34 and the imaging areas of the CCD device 33 which are disposed in the X-ray image detector 3. It is assumed that the image of the secondary slit 34 is formed on the imaging area of one or more CCD devices 33. In this case, the imaging scale is 1:nx in x-direction or a direction perpendicular to the longitudinal direction of the secondary slit 34, and 1:ny in y-direction. The secondary slit 34 has a width of about 5 mm, and the CCD device 33 which is presently available has an imaging area of 8 mm. In the example, therefore, nx=1. In accordance with the number and size of image sensors to be used, the imaging scale ny in the longitudinal direction of the slit may be set to be from 1 to about 20.

Pixels in a CCD imaging area plane having a size of a b (a=row interval, b=column interval) correspond to pixels of (nx×a) (ny×b) on the secondary slit plane. In the general views of FIGS. 7 and 8, therefore, 1 to n optical pixels in the secondary slit correspond to 1 to n charge pixels in the CCD device. In the longitudinal direction of the secondary slit, similarity is established. Therefore, an image of one straight line in the direction of the secondary slit is formed on one CCD line.

When suitable clock pulses are applied from the CCD driving circuit 23 as shown in FIG. 5, the image is transferred from an imaging area 33a to a storage area 33b, and then read out via a shift register 33c. The read out image is supplied to the A/D converter 25. In normal operation, the image accumulation period at the standard clock pulse rate of the CCD device is about 20 ms. After a lapse of the period, the image is supplied to the storage area in synchronization with clock pulses. Consequently, clock pulses the number of which is equal to the number of the rows of the CCD device are required. On the basis of the CCD format having 300 rows and the pulse period of 2 μs, therefore, the imaging area becomes empty after a lapse of about 0.6 ms, and a new image can be immediately taken.

The optical image generated in the scintillator 31 is formed on the CCD device 33, and the generated charge image is supplied at a predetermined clock pulse rate from the imaging area to the storage area in synchronization with the clock pulses. In this case, the image is read out in the unit of one row via the shift register in synchronization with the clock pulses, whereby the image information is accumulated. The clock pulse rate is selected so that, when converted onto the secondary slit plane, the speed of the charge image in x-direction is equal to that of the conventional tomography using a film.

As shown in FIG. 8, the CCD device 33 is divided into columns b1 to bm. Charges of each column are transferred from one row to the next row, and then supplied to the storage area 33b or directly to the shift register 33c in synchronization with the clock pulses. The speed at which this process is conducted is set by the frequency of the transfer clock pulses. A tomographic plane an image of which can be sharply formed is given by the following expression:

$$f = v/a \cdot d/(L-d)$$

where d is the distance between the film and the object, L is the distance between the film and the X-ray source, v is the speed of the X-ray source in a direction perpendicular to the object, a is the width of a CCD row, and f is the frequency of the clock pulses.

Figure 9:
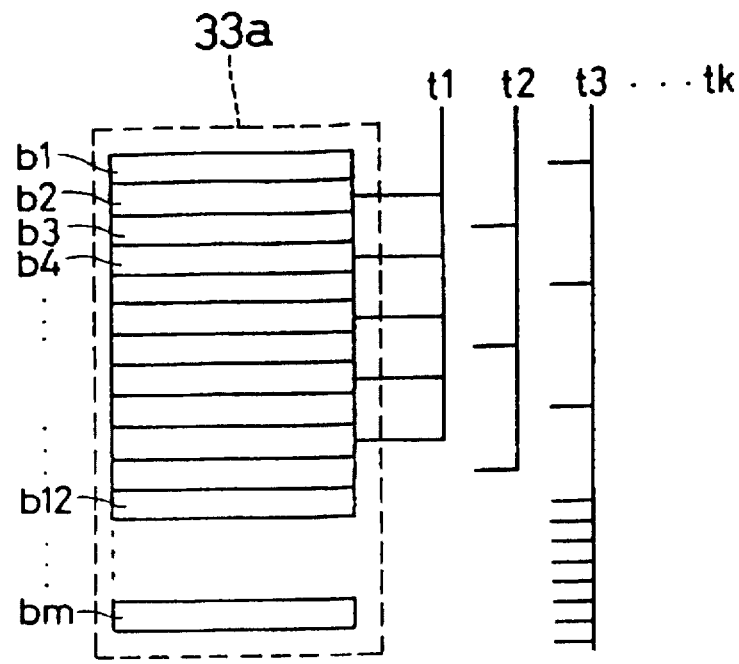
FIG. 9 is a diagram showing an example in which rows of the CCD are driven by different clock pulse frequencies.

FIG. 9 is a diagram showing an example in which the rows of the CCD are driven by different clock pulse frequencies. Among the CCD columns b1 to bm, several columns are controlled by different clock pulse frequencies t1 to tk. In this case, each clock pulse frequency corresponds to one imaging tomographic plane. The control can be conducted with being uniformly dispersed on the CCD device. In FIG. 9, the columns b2, b4, b6, b8, and b10 are controlled by a clock pulse frequency t1, the columns b3, b7, and b11 are controlled by a clock pulse frequency t2, and the columns b1, b5, b9, b12, ... are controlled by a clock pulse frequency t3. This means that, in the upper portion of a CCD element, the columns are controlled by clock pulse frequencies respectively corresponding to three different tomographic planes, and the columns subsequent to the twelfth column of the device are controlled only by a single clock pulse frequency. In the example of FIG. 9, therefore, three different tomographic planes respectively corresponding to the clock pulse frequencies t1, t2, and t3 can be detected in the upper image portion. By contrast, in the lower image portion, only an image of one tomographic plane, i.e., a tomographic plane corresponding to the clock pulse frequency t3 is formed.

In this way, when the columns of the CCD are controlled by different clock pulse frequencies, tomographic images respectively corresponding to plural tomographic planes can be simultaneously formed.

Next the process of removing blur from the tomographic images will be described.

Figure 10:
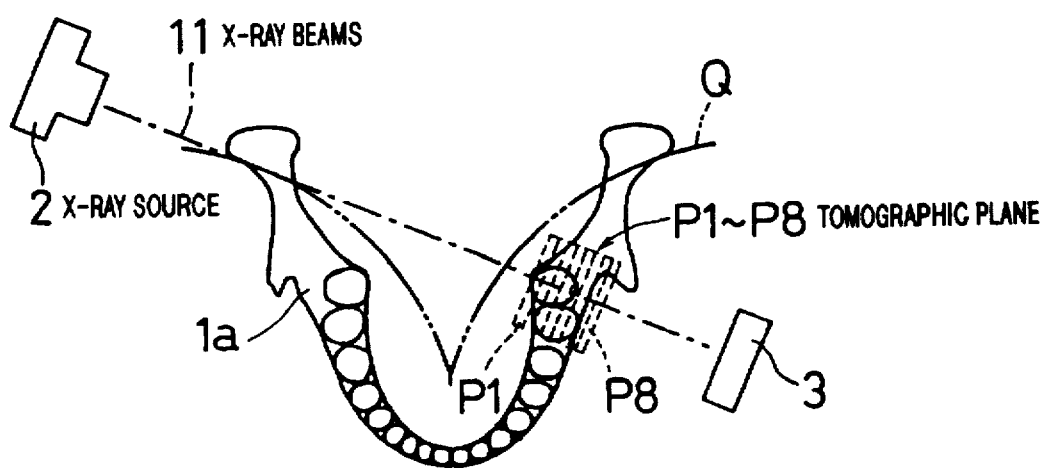
FIG. 10 is a diagram illustrating the principle of the panagraphy used in the invention.

FIG. 10 is a diagram illustrating the principle of the panagraphy used in the invention. The X-ray source 2 is placed on the back side of the head with respect to the mandibula 1a which has a substantially U-like shape. The X-ray beams 11 which are wide so that the horizontal width is increased to about 10 to 30 mm in the portion to be imaged perpendicularly enter the portion to be imaged or the dental arch. The X-ray image detector 3 is placed on the side of the face so as to receive the X-ray beams 11 which have passed through the portion to be imaged. The X-ray source 2 and the X-ray image detector 3 are integrally swiveled and the swiveling center is moved along a curved orbit Q as shown in FIG. 10.

Figure 11:
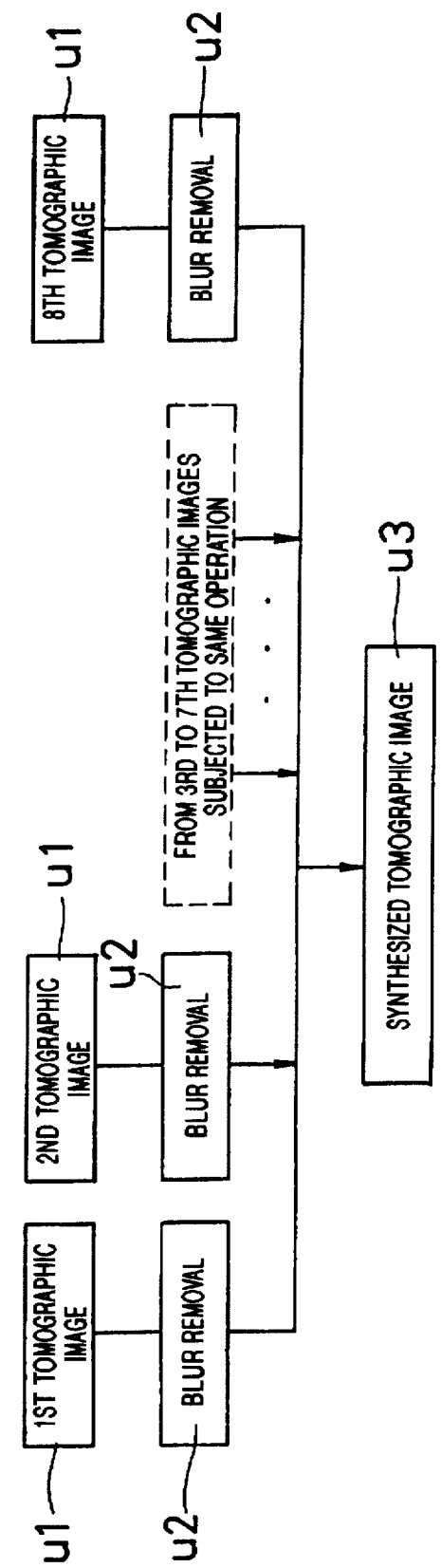
FIG. 11 is a flowchart showing a process of removing blur according to the invention.

FIG. 11 is a flowchart showing a process of removing blur according to the invention. On the basis of the image information detected by the X-ray image detector 3, according to the above-described technique, tomographic images which are eight in total and correspond to plural tomographic planes arranged at predetermined intervals along the X-ray irradiation direction, for example, eight tomographic planes P1 to P8 shown in FIG. 10 are calculated (step u1).

Next, attention is paid to a specific one of the eight tomographic images, and a convolution process is conducted by using image information of one or more of the tomographic images, thereby removing blur from the specific tomographic image (step u2).

Furthermore, the blur removal is conducted on two or more of the tomographic images, and the tomographic images from which blur is removed are summed each other so as to obtain a final synthesized tomographic image (step u3).

Next, a specific example of the positions of the tomographic images will be described. The X-ray image detector 3 is configured by plural light receiving pixels. In the tomographic image which is, for example, more inward than the center tomographic image by one image, therefore, one pixel is reduced in each of the sides, or two pixels in total are reduced in both sides. In this way, as moving to the inner side one by one, the number of pixels constituting the respective tomographic images is decremented by two. By contrast, as moving to the outer side one by one, the number of pixels constituting the respective tomographic images is incremented by two. It is assumed that the distance between the swivel center and the portion to be imaged is 50 mm and the secondary slit of the X-ray image detector 3 has a width corresponding to 40 pixels (in the case where the size of one pixel is set to be 0.25 mm and the width of the secondary slit to be 10 mm). When the center tomographic image is set as the reference, the positions of the tomographic planes can be expressed as follows:

The plane which is more outward than the center by two is positioned at 44/40×50 mm=55 mm.

The plane which is more outward than the center by one is positioned at 42/40×50 mm=52.5 mm.

The center plane is positioned at 40/40×50 mm=50 mm.

The plane which is more inward than the center by one is positioned at 38/40×50 mm=47.5 mm.

The plane which is more inward than the center by two is positioned at 36/40×50 mm=45 mm.

These relationships are based on the assumption that the X-ray beams are parallel to each other. When the X-ray beams are widened into a sector form, consideration is given to the magnification factor. In this way, the intervals of the tomographic planes are changed in accordance with the number of pixels in the X-ray image detector 3.

Next, the degree of blur in the image of each tomographic plane will be described. It is assumed that a point A which is free from blur exists on the center tomographic plane. In the tomographic plane which is more inward than the center by one, the point A is on three pixels and results in a blurred image. If the density of the original point A in the center is indicated by $D_0$, the density $D_{-1}$ of the blurred image is equally divided by three or $D_{-1} = D_0/3$.

In the tomographic plane which is more inward than the center by two, the point A appears as a blurred image existing on five pixels. If the density of the original point A in the center is indicated by $D_0$, the density $D_{-2}$ of the blurred image is equally divided by five or $D_{-2} = D_0/5$.

In this way, the density relationships between a blurred image and the original image are clarified. Then, the blurred image can be removed by tracing back the calculation.

Next, the removal of blur will be described.

When the expression $D_{-1}=D_0/3$ is modified, $3\times D_{-1}=D_0$ is obtained. When the densities of the blurred points in the tomographic plane which is more inward than the center by one are indicated by $D_{-1-1}$, $D_{-10}$, and $D_{-11}$, the following is attained:

$$D_{-1-1}+D_{-10}+D_{-11}=D_0$$

Similarly, also in the tomographic plane which is more outward than the center by one, the following is attained:

$$D_{+1-1}+D_{+10}+D_{+11}=D_0$$

The point and the density $D_{-10}$ in the plane which is more inward than the center by one appear as a blurred image at $D_{0-1}$, $D_{00}$, and $D_{01}$ in the center. As a result, at the point A (density $D_{00}$), the density which is ⅓ of $D_{-10}$ of the point is overlapped as blur. If only the point is blurred, the following is attained:

$$D_{00}=D_{-10}/3.$$

Similarly, since the density $D_{-1-1}$ of the adjacent point is overlapped, the following is attained:

$$D_{00}=D_{-1-1}/3.$$

As a result, the point receives ⅓ of blur from each of the three points in the inner plane, and hence $$D_{00}=(D_{0-1}+D_{00}+D_{01})/3.$$

Since the point receives blur also from the three points in the outer plane, moreover, the blur is added, and then the following is attained:

$$D_{00}=\{(D_{0-1}+D_{00}+D_{01})+(D_{+1-1}+D_{+10}+D_{+11})\}/3.$$

As described above, ⅓ of blur is added to the point A from each of the six points. Consequently, blur can be removed from the point A by subtracting the densities originating from the six points. In the six points, also the blur at the point A appears (each point contains ⅓ of $D_{00}$, and six points in total are accumulated, with the result that $D_{00}/3\times 6=2\times D_{00}$). When subtraction is simply conducted, therefore, excessive subtraction corresponding to $2\times D_{00}$ occurs. The density D of the point A without blur is:

$$D=D_{00}-(D_{0-1}+D_{00}+D_{01}+D_{+1-1}+D_{+11})/3.$$

When it is corrected by $2\times D_{00}$ which has been excessively subtracted, the density becomes as follows:

$$D=3\times D_{00}-(D_{0-1}+D_{00}D_{01}+D_{+1-1}+D_{+10}+D_{+11})/3.$$

By correctly rewriting this expression, the following expression is obtained:

$$D(X,Y)=D(X,Y)\times 3-(D(X+1,Y+1)+D(X,Y+1)+D(X-1,Y+1)+D(X+1,Y-1)+D(X,Y-1)+D(X-1,Y-1))/3$$

where (X, Y) indicates (column, line).

Next, a specific example of a convolution process will be described. For example, each tomographic image consists of m pixels in lateral and n pixels in vertical. The data of the tomographic image which is the first image counted from the innermost side are indicated by d(1, 1, 1) ... d(1, m, n), the data of the second tomographic image are indicated by d(2, 1, 1) ... d(2, m, n), and the data of a k-th tomographic image are similarly indicated by d(k, 1, 1) ... d(k, m, n).

Hereinafter, in the case where the second image (k=2) is considered as a specific tomographic image and a convolution process using the preceding and succeeding tomographic images (k=1 and 3) is conducted will be described. The convolution function can be expressed as a determinant as follows:

[Ex. 1]
$$\begin{pmatrix} -1/3 & -1/3 & -1/3 \\ 0 & 3 & 0 \\ -1/3 & -1/3 & -1/3 \end{pmatrix} \quad (1)$$

When expression (1) is normalized, the following expression is obtained:

[Ex. 2]
$$3\cdot \begin{pmatrix} -1/9 & -1/9 & -1/9 \\ 0 & 1 & 0 \\ -1/9 & -1/9 & -1/9 \end{pmatrix} \quad (2)$$

Then, the pixel density D(m, n) of a tomographic image without blur can be expressed as follows:

$$D(m,n)=3\cdot\{d(2,m,n)-\tfrac{1}{9}[d(1,m-1,n)+d(1,m,n)+d(1,m+1,n)+d(3,m-1,n)+d(3,m,n)+d(3,m+1,n)]\} \quad (3)$$

When D(m, n) is calculated with respect to m from 1 to m−1 and n from 0 to n, one tomographic image in which blur is removed can be obtained.

In the example described above, the 3×3-determinant is used. A 5×5-determinant or a 7×7-determinant can be expanded in the following manner:

[Ex. 3]
$$\begin{pmatrix} -1/5 & -1/5 & -1/5 & -1/5 & -1/5 \\ 0 & -1/3 & -1/3 & -1/3 & 0 \\ 0 & 0 & 5 & 0 & 0 \\ 0 & -1/3 & -1/3 & -1/3 & 0 \\ -1/5 & -1/5 & -1/5 & -1/5 & -1/5 \end{pmatrix} \quad (4)$$

$$\begin{pmatrix} -1/7 & -1/7 & -1/7 & -1/7 & -1/7 & -1/7 & -1/7 \\ 0 & -1/5 & -1/5 & -1/5 & -1/5 & -1/5 & 0 \\ 0 & 0 & -1/3 & -1/3 & -1/3 & 0 & 0 \\ 0 & 0 & 0 & 7 & 0 & 0 & 0 \\ 0 & 0 & -1/3 & -1/3 & -1/3 & 0 & 0 \\ 0 & -1/5 & -1/5 & -1/5 & -1/5 & -1/5 & 0 \\ -1/7 & -1/7 & -1/7 & -1/7 & -1/7 & -1/7 & -1/7 \end{pmatrix} \quad (5)$$

In the above, the coefficients ⅓, ⅕, and ⅐ are merely examples of execution. In practice, it is preferable to conduct correction with weighting such coefficients. Therefore, the convolution function has the following general form of:

[Ex. 4]

$$\begin{pmatrix} a(0,0), & a(1,0), & a(2,0), & \ldots & a(n,0) \\ \cdot & \cdot & \cdot & & \\ \cdot & \cdot & \cdot & & \\ \cdot & \cdot & \cdot & & \\ a(0,m), & a(1,m), & a(2,m), & \ldots & a(n,m) \end{pmatrix} \quad (6)$$

In the above, n and m are odd numbers such as 3, 5, 7, . . . The coefficient of a(n, m) must be determined or the weighting must be conducted while observing an actual image of the object.

In this way, the removal of blur can be conducted on the third tomographic image by using the first to fifth tomographic images, the removal of blur can be conducted on the fourth tomographic image by using the second to sixth tomographic images, and the removal of blur can be conducted on the fifth tomographic image by using the third to seventh tomographic images. Ideally, it is preferably to conduct the removal of blur by using not only the preceding two tomographic images and the succeeding two tomographic images but also preceding and succeeding ten to twenty tomographic images. With respect to a tooth, the dentition, or the jawbone, it is sufficient to take an image of a portion having a width of 10 mm. Considering the time required for conducting the process and the memory capacity, the number of images to be used is to be determined.

FIG. 12 is a flowchart showing a specific example of the process of removing blur according to the invention. In this example, three images without blur are prepared by using five tomographic images and then subjected to summing synthesization.

First, the normalization of the horizontal magnification factor will be described. In five tomographic images in total, i.e., the center tomographic image, the outer first and second tomographic images, and the inner first and second tomographic images, the horizontal magnification factors are different from each other because the positions of the tomographic planes are different from each other. Consequently, correction is performed so as to equalize the horizontal pixel numbers.

When the center tomographic image consists of 1,000 pixels in lateral and 500 pixels in vertical, for example, the horizontal pixel number of the tomographic image which is more outward than the center by one is output as 1,000×(42/40)=1,050. In the above, it is assumed that the width of the secondary slit of the X-ray detector corresponds to 40 pixels. Consequently, the horizontal magnification factor is 42/40.

In order to make the horizontal pixel number coincident with that of the center tomographic image, therefore, the horizontal pixel number is multiplied with the reciprocal of the horizontal magnification factor, i.e., 40/42 so as to be corrected to 1,050×(40/42)=1,000 pixels. Similarly, the horizontal pixel number of the tomographic image which is more outward than the center by two is output as 1,000× 44/40)=1,100, and hence the horizontal pixel number is multiplied with the reciprocal of the horizontal magnification factor, i.e., 40/44 so as to be corrected to 1,100×(40/44)=1,000 pixels. By contrast, the horizontal pixel number of the tomographic image which is more inward than the center by one is output as 1,000×(38/40)=950, and hence the horizontal pixel number is multiplied with the reciprocal of the horizontal magnification factor, i.e., 40/38 so as to be corrected to 950×(40/38)=1,000 pixels. The horizontal pixel number of the tomographic image which is more inward than the center by two is output as 1,000×36/40)=900, and hence the horizontal pixel number is multiplied with the reciprocal of the horizontal magnification factor, i.e., 40/36 so as to be corrected to 900×(40/36)=1,000 pixels.

Thereafter, a convolution process or a frequency process is executed by using three tomographic images, i.e., the outer two ones and the center one among the five tomographic images which have been subjected to the normalization of the horizontal magnification factor. As a result, an image without blur I1 is obtained. Furthermore, a convolution process or a frequency process is executed by using three tomographic images, i.e., the center one, the outer first one, and the inner first one, with the result that an image without blur I2 is obtained, and a convolution process or a frequency process is executed by using three tomographic images, i.e., the center one and the inner two ones, with the result that an image without blur I3 is obtained.

Thereafter, the images without blur I1 to I3 are summed each other and a synthesized tomographic image without blur is obtained.

In the above, the example in which one image without blur can be obtained by using three tomographic images has been described. Alternatively, one image without blur may be calculated from five, seven or more tomographic images.

As described above in detail, according to the invention, a convolution process is conducted by using plural tomographic images, whereby a tomographic image which is free from blur can be obtained. In the case where an X-ray imaging process is conducted by using wide X-ray beams, even when tomographic images are blurred, therefore, a clear tomographic image can be obtained by the above-mentioned removal of blur.

The use of wide X-ray beams produces advantages such as: 1) influences of obstruction shadows such as the vertebrae cervicales can be reduced; 2) the use efficiency of X-rays is improved and the current of an X-ray tube can be reduced, thereby lowering the burden of the X-ray tube; and 3) X-ray detecting means having a large imaging area can be used and hence the imaging efficiency is improved.

When tomographic images from which blur is removed are summed each other to obtain a synthesized tomographic image, it is possible to obtain an X-ray tomographic image which has a reduced level of noises and higher sharpness.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A dental panoramic X-ray imaging apparatus comprising:

an X-ray source for irradiating an object with X-rays;

X-ray image detecting means for detecting an image of X-rays which have passed through the object;

swivel means for integrally swiveling the X-ray source and the X-ray detecting means around the object;

image storing means for storing image information output from the X-ray detecting means during a period when the swivel means operates; and image processing means for on the basis of image information stored in the image storing means, forming a tomographic image along a desired tomographic plane and conducting a calculation process on the tomographic image, wherein plural tomographic images corresponding to plural tomographic planes which are arranged at predetermined intervals along a direction of the X-ray irradiation are calculated, a convolution process or a frequency process is conducted on a specific tomographic image by using image information of at least one of the tomographic images, and thereby blur from the specific tomographic image is removed.

2. The dental panoramic X-ray imaging apparatus according to claim 1, wherein removal of blur is conducted on two or more images of the tomographic images, and the tomographic images from which blur has been removed are summed each other to obtain a synthesized tomographic image.

* * * * *